United States Patent
Maeda

(10) Patent No.: US 10,285,594 B2
(45) Date of Patent: May 14, 2019

(54) ELECTRIC MOTOR CAPABLE OF REDUCING COGGING TORQUE

(71) Applicant: FANUC CORPORATION, Yamanashi (JP)

(72) Inventor: Takuya Maeda, Yamanashi (JP)

(73) Assignee: FANUC CORPORATION, Yamanashi (JP)

(*) Notice: Subject to any disclaimer, the term of this patent is extended or adjusted under 35 U.S.C. 154(b) by 0 days.

(21) Appl. No.: 15/699,005

(22) Filed: Sep. 8, 2017

(65) Prior Publication Data

US 2018/0020923 A1    Jan. 25, 2018

Related U.S. Application Data

(63) Continuation of application No. 14/509,170, filed on Oct. 8, 2014, now abandoned.

(30) Foreign Application Priority Data

Oct. 11, 2013  (JP) .................. 2013-213736

(51) Int. Cl.
*H02K 1/27* (2006.01)
*H02K 21/12* (2006.01)
(Continued)

(52) U.S. Cl.
CPC .......... *A61B 5/0066* (2013.01); *A61B 3/0025* (2013.01); *A61B 3/102* (2013.01);
(Continued)

(58) Field of Classification Search
CPC .... H02K 1/2706; H02K 1/2773; H02K 21/14; H02K 29/03; H02K 1/276; H02K 1/2766; H02K 21/12

USPC .... 310/216.074, 216.088, 216.091, 216.092, 310/216.094, 156.53, 156.56, 156.38, 310/156.43–156.48
See application file for complete search history.

(56) References Cited

U.S. PATENT DOCUMENTS

2006/0017345 A1*  1/2006  Uchida ............... H02K 1/2766
                                                                310/156.56

FOREIGN PATENT DOCUMENTS

CN          1713483 A      12/2005
CN       203193413 U       9/2013
(Continued)

OTHER PUBLICATIONS

JP 2010178489 A (English Translation).*
(Continued)

*Primary Examiner* — Thomas Truong
*Assistant Examiner* — Alexander Moraza
(74) *Attorney, Agent, or Firm* — Fredrikson & Byron, P.A.

(57) ABSTRACT

An electric motor including a rotor including magnetic pole units and a stator including slots facing an outer peripheral surface of the rotor. Each of the magnetic pole units is bulged to an outside in a radial direction so that a waveform of a magnetic flux density generated from the rotor is a sine wave shape, and a concave part or convex part which is small enough to prevent changing of a waveform cycle of cogging torque determined by a least common multiple of the number of slots and the number of magnetic poles of the rotor, is formed at a central part in a circumferential direction of an outer peripheral surface in each of the magnetic pole units.

4 Claims, 14 Drawing Sheets

(51) Int. Cl.
  *H02K 21/14*  (2006.01)
  *H02K 29/03*  (2006.01)
  *A61B 3/00*  (2006.01)
  *A61B 5/00*  (2006.01)
  *H02K 1/16*  (2006.01)
  *H02K 1/24*  (2006.01)
  *A61B 3/10*  (2006.01)
  *G01B 9/02*  (2006.01)

(52) U.S. Cl.
  CPC ..... *G01B 9/02044* (2013.01); *G01B 9/02084* (2013.01); *G01B 9/02091* (2013.01); *H02K 1/16* (2013.01); *H02K 1/24* (2013.01); *H02K 1/2773* (2013.01); *A61B 2562/0233* (2013.01); *A61B 2576/00* (2013.01); *H02K 1/2706* (2013.01); *H02K 29/03* (2013.01); *H02K 2213/03* (2013.01)

(56) References Cited

FOREIGN PATENT DOCUMENTS

| | | | |
|---|---|---|---|
| CN | 204179778 | U | 2/2015 |
| DE | 60304937 | T2 | 10/2006 |
| FR | 4784815 | A1 | 4/2000 |
| JP | 11164501 | A | 6/1999 |
| JP | 2002010541 | A | 1/2002 |
| JP | 2003023740 | A | 1/2003 |
| JP | 2003061326 | A | 2/2003 |
| JP | 2004056871 | A | 2/2004 |
| JP | 2004064857 | A | 2/2004 |
| JP | 2006014457 | A | 1/2006 |
| JP | 2006109590 | A | 4/2006 |
| JP | 2010094001 | A | 4/2010 |
| JP | 2010166683 | A | 7/2010 |
| JP | 2010178489 | A * | 8/2010 |
| JP | 2011061998 | A | 3/2011 |
| JP | 2012517209 | A | 7/2012 |
| JP | 2012210033 | A | 10/2012 |
| JP | 2012244641 | A | 12/2012 |
| WO | 8300956 | A1 | 3/1983 |

OTHER PUBLICATIONS

English Abstract for Japanese Publication No. 2003-023740 A, published Jan. 24, 2003, 1 pg.
English Abstract for Japanese Publication No. 11-164501 A, published Jun. 18, 1999, 1 pg.
English Machine Translation for Japanese Publication No. 2012-244641 A, published Dec. 10, 2012, 23 pgs.
English Machine Translation for Japanese Publication No. 2002-010541 A, published Jan. 11, 2002, 8 pgs.
English Machine Translation for Japanese Publication No. 2003-061326 A, published Feb. 28, 2003, 33 pgs.
English Machine Translation for Japanese Publication No. 2004-056871 A, published Feb. 19, 2004, 20 pgs.
English Machine Translation for Japanese Publication No. 2004-064857 A, published Feb. 26, 2004, 16 pgs.
English Machine Translation for Japanese Publication No. 2006-014457 A, published Jan. 12, 2006, 13 pgs.
English Machine Translation for Japanese Publication No. 2006-109590 A, published Apr. 20, 2006, 8 pgs.
English Machine Translation for Japanese Publication No. 2010-094001 A, published Apr. 22, 2010, 17 pgs.
English Machine Translation for Japanese Publication No. 2010-166683 A, published Jul. 29, 2010, 10 pgs.
English Machine Translation for Japanese Publication No. 2010-178489 A, published Aug. 12, 2010, 20 pgs.
English Machine Translation for Japanese Publication No. 2012-210033 A, published Oct. 25, 2012, 13 pgs.
English Machine Translation for Japanese Publication No. 2012-517209 A, published Jul. 26, 2012, 16 pgs.
English Machine Translation for Japanese Publication No. 2011-061998 A, published Mar. 24, 2011, 37 pgs.
English Abstract and Machine Translation for German Publication No. 60304937 T2, published Oct. 26, 2006, 8 pgs.
English Abstract and Machine Translation for French Publication No. 2784815 A1, published Apr. 21, 2000, 9 pgs.
English Abstract and Machine Translation for Chinese Publication No. 204179778 U, published Feb. 25, 2015, 15 pgs.
English Abstract for Chinese Publication No. 1713483 A, published Dec. 28, 2015, 1 pg.
English Abstract for Chinese Publication No. 203193413 U, published Sep. 11, 2013, 1 pg.

* cited by examiner

ELECTRIC MOTOR CAPABLE OF REDUCING COGGING TORQUE

RELATED APPLICATIONS

This is a continuation of application Ser. No. 15/509170, filed Oct. 8, 2014, which claims priority to Japanese Application No. 2013-213736, filed Oct. 11, 2013, the teachings of which are incorporated herein by reference.

BACKGROUND OF THE INVENTION

1. Field of the Invention

The present invention relates to an electric motor capable of reducing cogging torque.

2. Description of the Related Art

In a permanent magnet electric motor that includes a rotor having a permanent magnet, due to the presence of slots of a stator core facing an outer peripheral surface of the rotor, magnetic coenergy fluctuates during rotation of the rotor, and therefore generates cogging torque that is torque pulsation. The cogging torque is preferably reduced because the cogging torque interferes with smooth rotation of the rotor to generate sound or vibration. Conventionally, as an electric motor designed to reduce such cogging torque, there are known electric motors as described in Japanese Laid-open Patent Publication No. 2003-023740 (JP2003-023740A) and Japanese Laid-open Patent Publication No. 11-164501 (JP11-164501A).

A rotor of an electric motor described in JP2003-023740A includes a magnetic pole unit having a circular-arc outer peripheral surface bulged to an outside in a radial direction so that a waveform of a magnetic flux density generated from the rotor is a sine wave shape. Maximum outer diameter parts of the outer peripheral surface are arranged on both sides of a circumferential direction center (magnetic pole center) of the magnetic pole unit, and a concave part is formed in the circumferential direction center of the magnetic pole unit. This arrangement doubles the number of waveform peaks of cogging torque generated for each rotation of the rotor and reduces a magnitude of the cogging torque by half. On the other hand, JP11-164501A describes an electric motor in which an outer peripheral surface of a magnetic pole unit of a rotor is formed into a cylindrical shape around a rotary shaft of the rotor. This electric motor is configured such that a waveform of a magnetic flux density of the rotor is not a sine wave shape but a trapezoidal wave shape.

The electric motor described in JP2003-023740A is configured to reduce the magnitude of cogging torque by half, by substantially doubling the number of magnetic poles, but is unable to adjust the magnitude of the cogging torque to an arbitrary magnitude.

SUMMARY OF THE INVENTION

According to an aspect of the present invention, an electric motor includes a rotor including magnetic pole units, and a stator including slots facing an outer peripheral surface of the rotor. Each of the magnetic pole units is bulged to an outside in a radial direction so that a waveform of a magnetic flux density generated from the rotor is a sine wave shape. A concave part or convex part is formed at a central part in a circumferential direction of an outer peripheral surface in each of the magnetic pole units, and is small enough to prevent changing of a waveform period of cogging torque determined by a least common multiple of the number of slots and the number of magnetic poles of the rotor.

BRIEF DESCRIPTION OF THE DRAWINGS

The objects, features, and advantages of the present invention will become clearer from the following description of embodiments in relation to the attached drawings. In the attached drawings.

DETAILED DESCRIPTION

Figure 1:
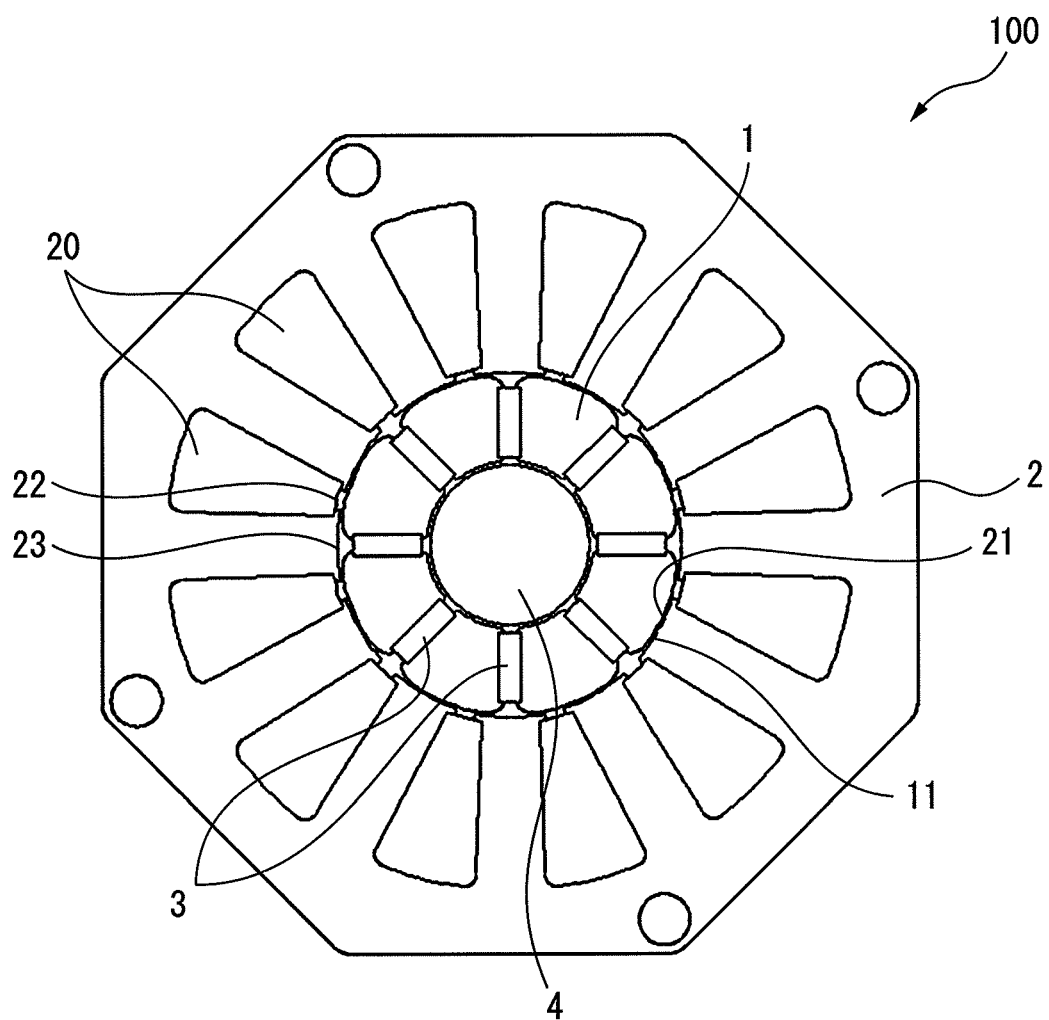
FIG. 1 is a sectional view schematically illustrating an internal configuration of an electric motor according to an embodiment of the present invention.

Hereinafter, the embodiments of the present invention will be described referring to FIGS. 1 to 21. FIG. 1 is a sectional view schematically illustrating an internal configuration of an electric motor 100 according to an embodiment of the present invention. The electric motor 100, which is a permanent magnet synchronous electric motor with eight poles and twelve slots, includes a rotor 1 provided with permanent magnets 3 and a stator 2 disposed around the rotor 1. An output shaft 4 is disposed at a center of the rotor 1.

Predetermined space is formed between an outer peripheral surface 11 of the rotor 1 and an inner peripheral surface 21 of the stator 2. In the inner peripheral surface 21 of the stator 2, slot openings 22 and teeth 23 are alternately formed in a circumferential direction. Slots 20 are formed on radial direction outsides of the slot openings 22. A coil is received in each slot 20. By supplying current to the coil, the stator 2 forms a rotating magnetic field, and the rotor 1 is rotated in synchronization with the rotating magnetic field.

Figure 2A:
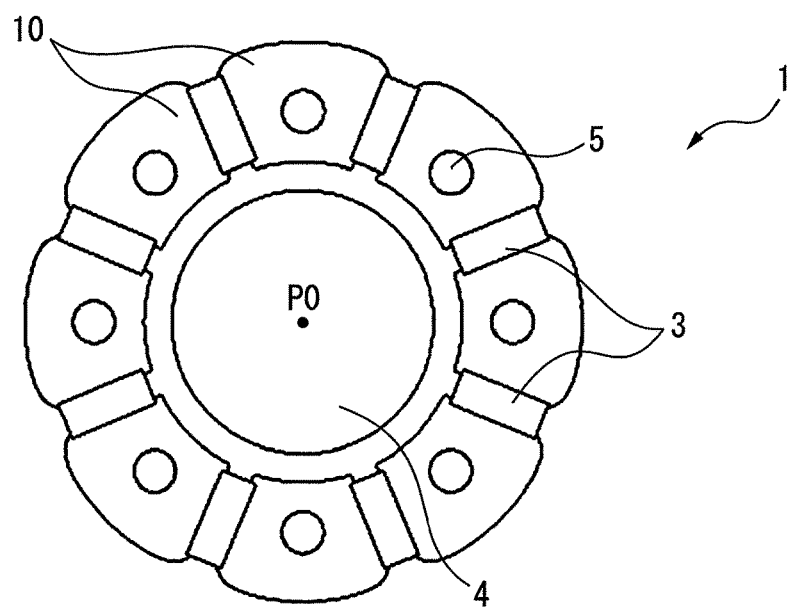
FIG. 2A is an enlarged view illustrating a rotor illustrated in FIG. 1.

FIG. 2A is an enlarged view illustrating the rotor 1. As illustrated in FIG. 2A, the eight permanent magnets 3 are radially arranged at equal intervals in a circumferential direction around a rotational center P0 of the rotor 1. Each yoke 10 is disposed between the permanent magnets 3, 3 adjacent to each other in the circumferential direction, and eight magnetic poles (magnetic pole units) having the same shape are formed by the yokes 10. The yokes 10 are configured by stacking a plurality of plate members in an axial direction and integrally fastening them via tie rods 5.

Figure 2B:
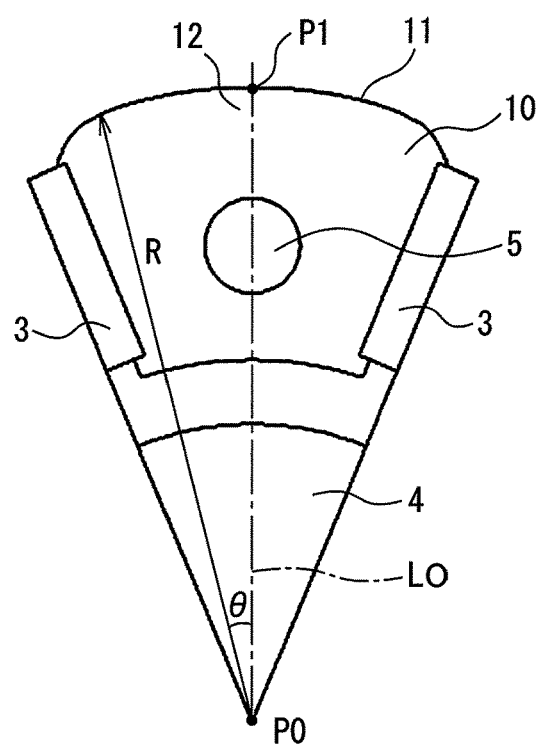
FIG. 2B is an enlarged view illustrating a configuration of one pole of the rotor illustrated in FIG. 2A.

FIG. 2B is an enlarged view illustrating a configuration of a single yoke 10, in other words, the rotor 1 of one pole, illustrated in FIG. 2A. In FIG. 2B, a central angle of the rotor 1 is 45°. The rotor 1 has a line-symmetrical shape in the circumferential direction with respect to a reference line L0 connecting the rotational center P0 with a circumferential-direction center (magnetic pole center P1) of an outer peripheral surface 11 of the yoke 10 by a straight line. The outer peripheral surface 11 of the yoke 10 is formed to bulge to an outside in a radial direction. Accordingly, a distance (rotor radius R) from the rotational center P0 to the outer peripheral surface 11 of the yoke 10 is smaller as an angle θ from the straight line L0 is larger. The rotor radius R is maximum at a magnetic pole central part 12 in which θ is 0°. An angle θ from the reference line L0 around the rotational center P0 is also referred to as a mechanical angle.

Figure 3:
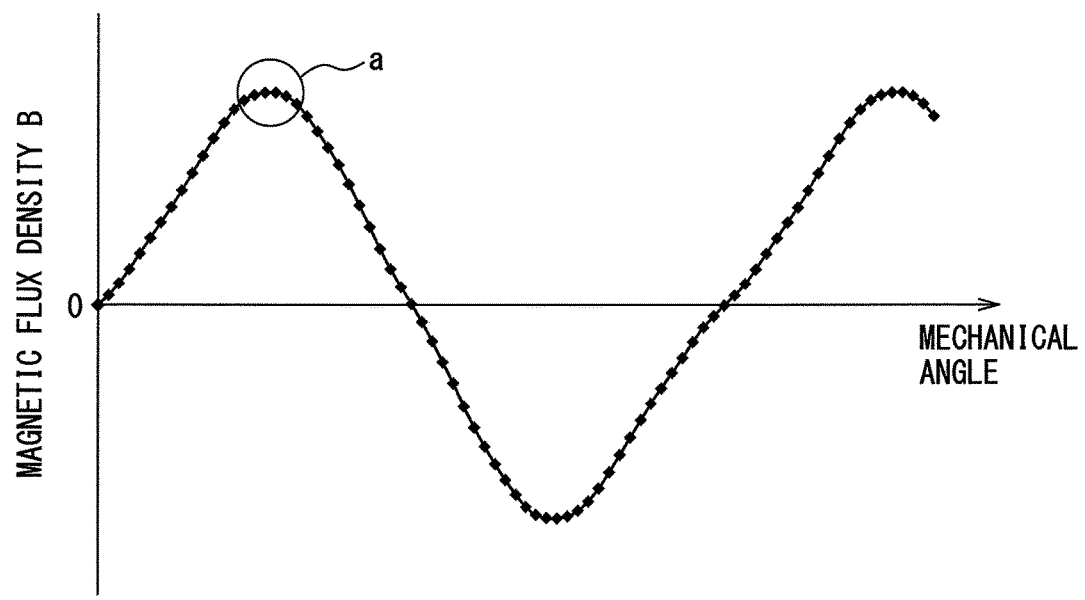
FIG. 3 is a diagram illustrating a waveform of a magnetic flux density when it is assumed that no slot opening is formed in an inner peripheral surface of a stator.

FIG. 3 is a diagram illustrating a waveform of a magnetic flux density B when it is assumed that no slot opening 22 is formed in an inner peripheral surface 21 of the stator 2. This waveform is obtained by disposing a cylinder around the rotor 1 and measuring a magnetic flux between the rotor 1 and the cylinder in a static state of the rotor 1. In FIG. 3, a horizontal axis indicates a mechanical angle of the rotor 1 while a vertical axis indicates a radial-direction component of the magnetic flux density B generated from the rotor 1. One cycle of the waveform corresponds to a mechanical angle 45°. In the embodiment, the rotor 1 has the outer peripheral surface 11 bulged to the radial direction outside. Thus, as illustrated in FIG. 3, the magnetic flux density B generated from the rotor 1 is a sine wave shape, and the magnetic flux concentrates at the magnetic pole central part 12 (illustrated as an in FIG.3).

Figure 4:
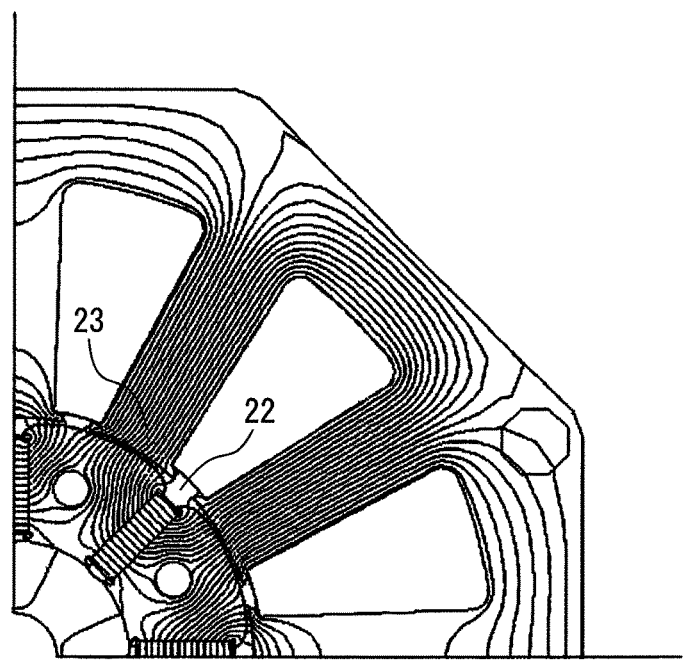
FIG. 4 is a diagram illustrating an example of magnetic flux lines in an electric motor.

The real electric motor 100 includes the slot openings 22 formed in the inner peripheral surface 21 of the stator 2. Thus, a difference is generated in magnetic permeability μ between the slot openings 22 and the teeth 23. In other words, magnetic permeability μ of the teeth 23 composed of an electromagnetic steel sheet is generally larger by 1000 times or more than magnetic permeability μ of the slot openings 22 determined by air and a coil (copper) in each slot 20. As a result, as illustrated in FIG. 4, the magnetic flux generated from the rotor 1 passes through the teeth 23 without passing through the slot openings 22 having high magnetic resistance. In other words, the magnetic flux is dense at the teeth 23, thus generating a coarse/fine distribution of the magnetic flux density B in the circumferential direction.

Figure 5:
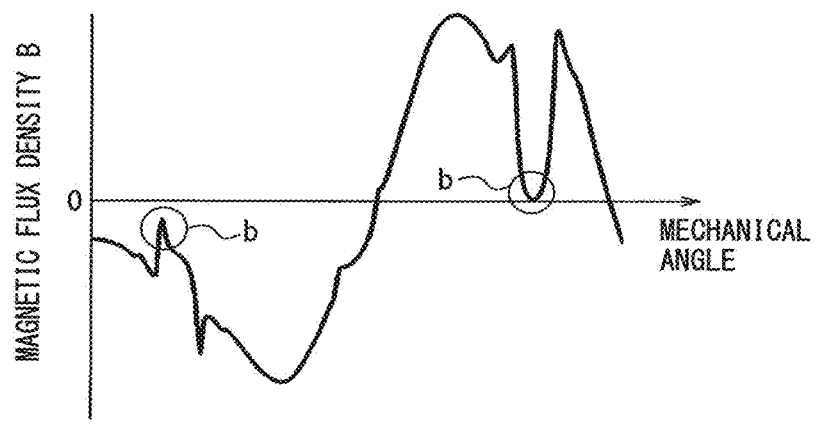
FIG. 5 is a diagram illustrating a waveform of a magnetic flux density when a slot opening is formed in the inner peripheral surface of the stator.

A physical amount obtained by magnetic flux density B×B/ magnetic permeability μ is referred to as magnetic coenergy. When the magnetic pole central part 12 sequentially passes through the vicinities of the slot openings 22 and the teeth 23 with rotation of the rotor 1, the magnetic coenergy of the magnetic pole central part 12 fluctuates, thus generating cogging torque that is torque pulsation. A generation status of the cogging torque will be described specifically. FIG. 5 is a diagram illustrating a waveform of the magnetic flux density B when slot openings 22 are formed in the inner peripheral surface 21 of the stator 2.

As illustrated in FIG. 5, at a position where the rotor 1 faces any of the slot openings 22 ("b" illustrated in FIG. 5), the sine wave shape is broken, and the magnetic flux density B approaches 0. The magnetic coenergy accordingly fluctuates to generate cogging torque. The cogging torque is generated by a number of times equal to a least common multiple of the number of slots and the number of magnetic poles for each rotation of the rotor 1 (for example, twenty four times for the case of eight poles and twelve slots), and a mechanical angle of a cycle of the cogging torque is 15° (=360°/24). The cogging torque is preferably reduced because it interferes with smooth rotation of the rotor 1 to generate sound or vibration. In the embodiment, to reduce such cogging torque, the magnetic pole central part 12 of the rotor 1 (yoke 10) where the magnetic flux concentrates is configured as described below.

Figure 6:
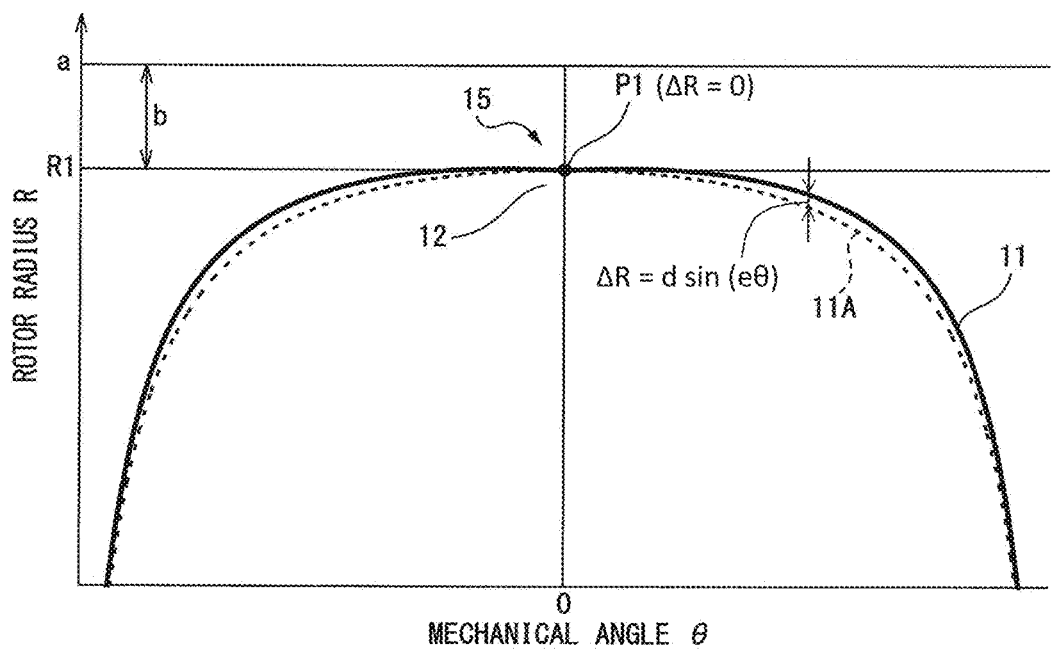
FIG. 6 is an enlarged view illustrating an outer peripheral surface shape of the rotor constituting the electric motor according to the embodiment of the present invention.

FIG. 6 is an enlarged view illustrating an outer peripheral shape of the yoke 10 constituting the electric motor 100 according to the embodiment of the present invention. A horizontal axis indicates an angle from the reference line L0 (illustrated in FIG. 2B), in other words, a mechanical angle θ, while a vertical axis indicates a distance from the rotational center P0 to the outer peripheral surface 11, in other words, a rotor radius R. In the embodiment, the outer peripheral surface 11 (indicated by a solid line) is set by adding a correction amount ΔR in the radial direction using a mechanical angle θ as a parameter to a reference surface 11A (indicated by dotted line) using a mechanical angle θ as a parameter.

The reference surface 11A is bulged to an outside in the radial direction so that the rotor radius R is maximum R1 at the magnetic pole center P1 of the mechanical angle 0°, and is formed into a circular arc shape as a whole. A waveform of the magnetic flux density B from the reference surface 11A has a sine wave shape as illustrated in FIG. 3 when the presence of the slots 20 is ignored. The rotor radius R of the reference surface 11A is set by the following formula (I):

$$R=a-b/\cos(C\theta) \qquad (I)$$

In the formula (I), "a" is a radius (stator inner diameter) of the inner peripheral surface 21 of the stator, "b" is a minimum gap between the rotor 1 and the stator 2, and c is a coefficient. The mechanical angle θ is set within a range of −7.5° to 7.5°.

The rotor radius R of the outer peripheral surface 11 is set by the following formula (II):

$$R=a-b/\cos(c\theta)+d\times\sin(e\theta) \qquad (II)$$

In the formula (II), d×sin(eθ) is a correction function indicating a correction amount ΔR, "d" is a maximum correction amount, and "e" is a coefficient indicating characteristics of the correction function. For example, the coefficient "e" is set so that eθ can be respectively 180° and −180° when the mechanical angle θ is maximum and minimum. At this time, the correction amount ΔR is 0.

By setting the correction amount ΔR based on the sine function as described above, the correction amount ΔR at the magnetic pole center P1 (θ=0) is 0, and the correction amount ΔR gradually increases with the increase of the mechanical angle θ. Accordingly, a tiny and smooth circular-arc concave part 15 is formed at the magnetic pole central part 12. A ratio b/a of the minimum gap "b" to the stator inner diameter "a" is, for example, about 1/10, and a ratio d/b of the maximum correction amount "d" to the minimum gap "b" is, for example, about 1/10. Thus, a ratio d/a of the maximum correction amount "d" to the stator inner diameter "a" is about 1/100, and the maximum correction amount "d" is considerably smaller than the stator inner diameter "a".

In this example, an absolute value of the maximum correction amount "d" is, for example, 0.1 mm or less. Visual checking of the presence of correction is consequently difficult. Checking can be performed by using a measuring device such as an optical projector. Strictly, the maximum correction amount "d" is set according to the size of the stator inner diameter "a" and the size of the minimum gap "b". The maximum correction amount "d" is larger as the stator inner diameter "a" and the minimum gap "b" are larger. For example, the maximum correction amount "d" is within a range of 0.01 mm to 0.1 mm.

Figure 7:
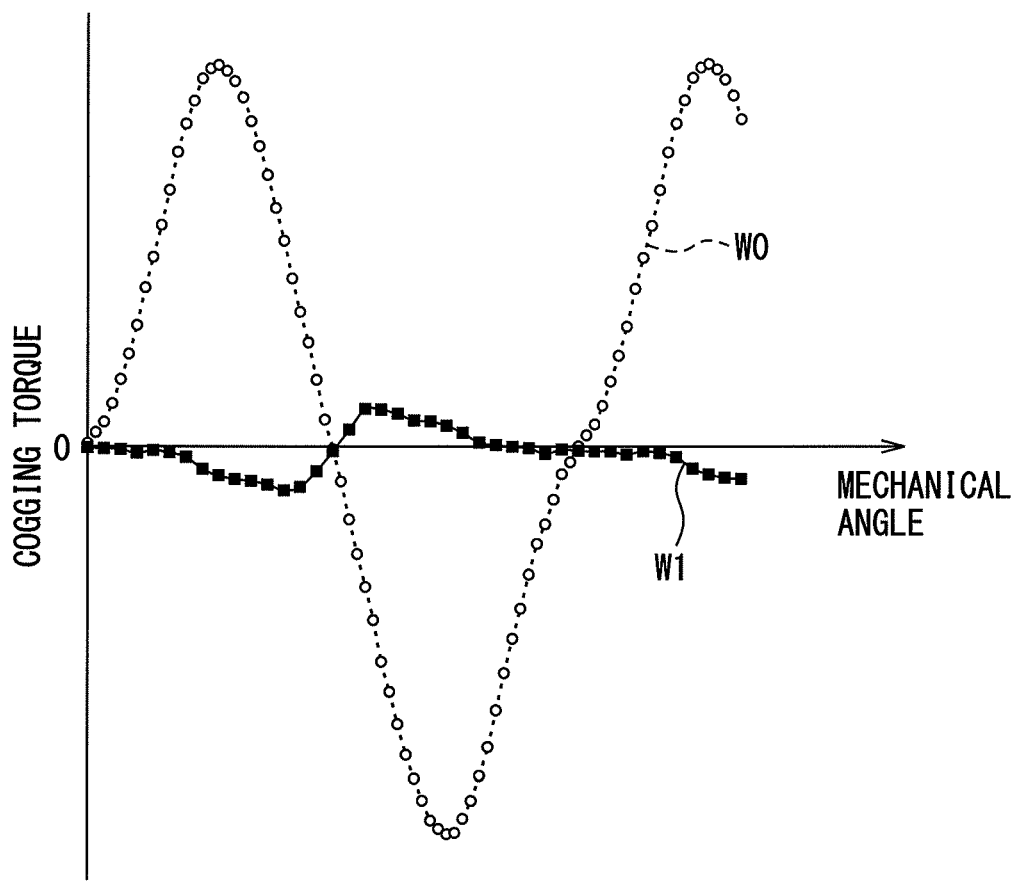
FIG. 7 is a diagram illustrating a change in waveform of cogging torque generated in the electric motor having the outer peripheral surface shape illustrated in FIG. 6.

FIG. 7 is a diagram illustrating a waveform of cogging torque. In FIG. 7, W0 is a waveform of cogging torque when no correction is performed for the reference surface 11A, in other words, when the rotor radius R is set along the dotted line illustrated in FIG. 6. W1 is a waveform of cogging torque when correction is performed for the reference surface 11A, in other words, when the rotor radius R is set along the solid line illustrated in FIG. 6. As illustrated in FIG. 7, the cogging torque indicated by the waveform W1 is smaller than that indicated by the waveform W0. Thus, a size of the cogging torque can be reduced by adding the correction amount ΔR to the rotor radius R of the reference surface 11A to form the tiny concave part 15 at the magnetic pole central part 12.

Figure 8:
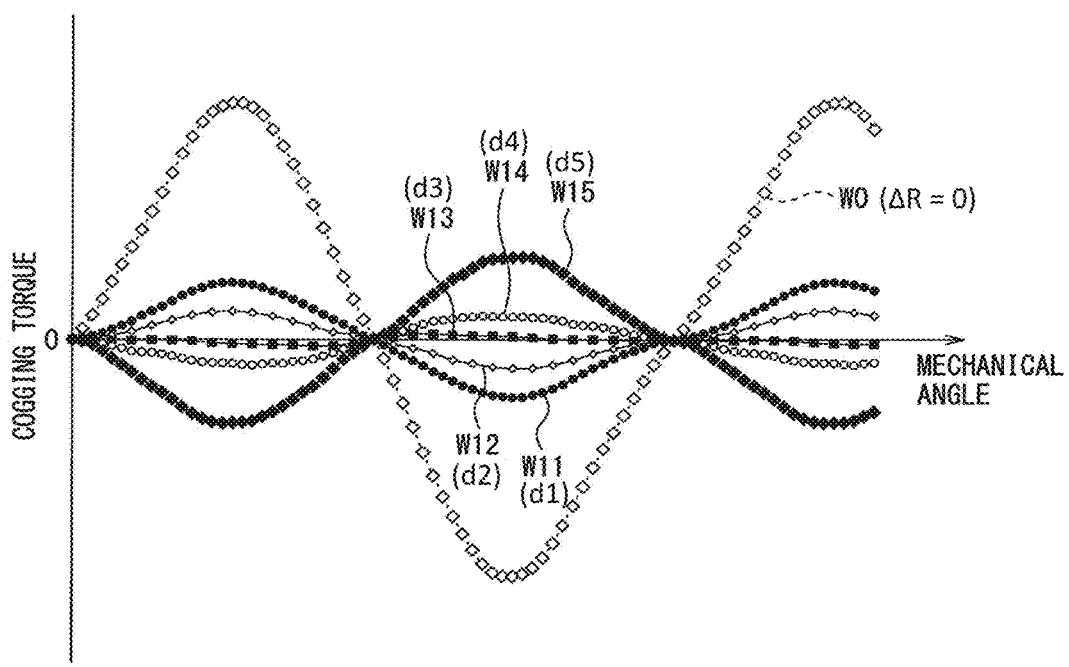
FIG. 8 is a diagram illustrating a change in waveform of cogging torque with changes of a maximum correction amount.

FIG. 8 is a diagram illustrating a change in waveform of cogging torque with changes of the maximum correction amount "d". Waveforms W11, W12, W13, W14, and W15 are waveforms of cogging toque corresponding to maximum correction amounts d1, d2, d3, d4, and d5, respectively. The maximum correction amounts d1 to d5 are set in a relationship of d1<d2<d3<d4<d5. As illustrated in FIG. 8, with the increase of the maximum correction amount "d", the cogging torque deviates from the waveform W0, and peak values of the cogging torque approach 0 (W11→W12→W13). When the maximum correction amount "d" increases more, waveforms (W14 and W15) of opposite phases are generated. Thus, by setting the maximum correction amount "d" to an optimal value, the cogging torque can be reduced to the utmost extent. In this case, the maximum correction amount "d" is very small (e.g., 0.1 mm or less). As a result, even when the maximum correction amount "d" is changed, no influence is given to the waveform cycle of the cogging toque, but only the magnitude of the cogging torque can be changed.

The present embodiment can provide the following operation effects.

(1) Each of the magnetic pole units (yokes 10) of the rotor 1 of the electric motor 100 is bulged to the radial direction outside so that the waveform of the magnetic flux density B generated from the rotor 1 is a sine wave shape (illustrated in FIG. 3), and the tiny concave part 15 (illustrated in FIG. 6) is formed at the central part in the circumferential direction (magnetic pole central part 12) of the outer peripheral surface 11 of the magnetic pole unit, which is small enough to prevent changing of the waveform cycle of the cogging torque determined by the least common multiple of the number of slots 20 and the number of magnetic poles of the rotor 1. Thus, the cogging torque can be greatly reduced while keeping the waveform cycle of the cogging torque constant.

Specifically, in a configuration where convex parts are formed on both sides of the magnetic pole center P1 to substantially double the number of magnetic poles of the rotor 1, the waveform cycle of the cogging torque is reduced to be about half. As a result, while the magnitude of the cogging torque would be about half, reduction of the magnitude of the cogging torque of more than half is difficult. On the other hand, as in the case of the embodiment, when the tiny concave part 15 visually indiscernible are formed at the magnetic pole center 12 where the magnetic flux concentrates, the magnitude of the cogging torque can be reduced to the utmost extent by appropriately adjusting the correction amount ΔR (maximum correction amount "d") determining the concave part 15.

Figure 9A:
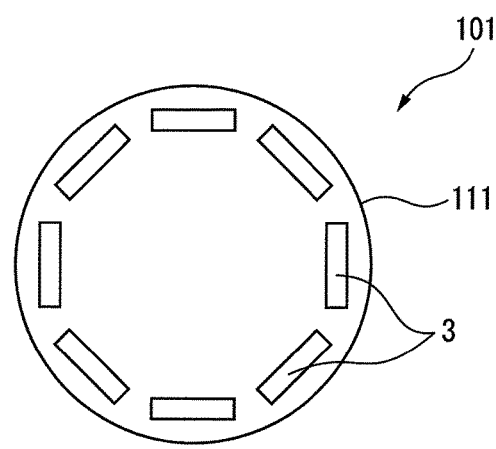
FIG. 9A is a diagram illustrating a rotor having a circular outer peripheral surface.

The aforementioned effect can be obtained in the case of the rotor 1 configured such that the rotor radius R of the reference surface 11A is maximum at the magnetic pole central part 12 and the waveform of the magnetic flux density generated from the rotor 1 exhibits the sine wave shape. For example, as illustrated in FIG. 9A, when an outer peripheral surface 111 of a rotor 101 has a circular shape, a waveform of a magnetic flux density B generated from the rotor 101 has a trapezoidal shape illustrated in FIG. 9B. FIG. 10 is a diagram illustrating a change in waveform of cogging torque when a correction amount ΔR is added to the reference surface 11A as in the aforementioned case, with the outer peripheral surface 111 of the rotor 101 set as the reference surface 11A. In FIG. 10, a waveform W100 is a waveform of cogging torque when no correction is performed for the reference surface 11A. Each of waveforms W101 and W102 is a waveform when correction is performed.

Figure 9B:
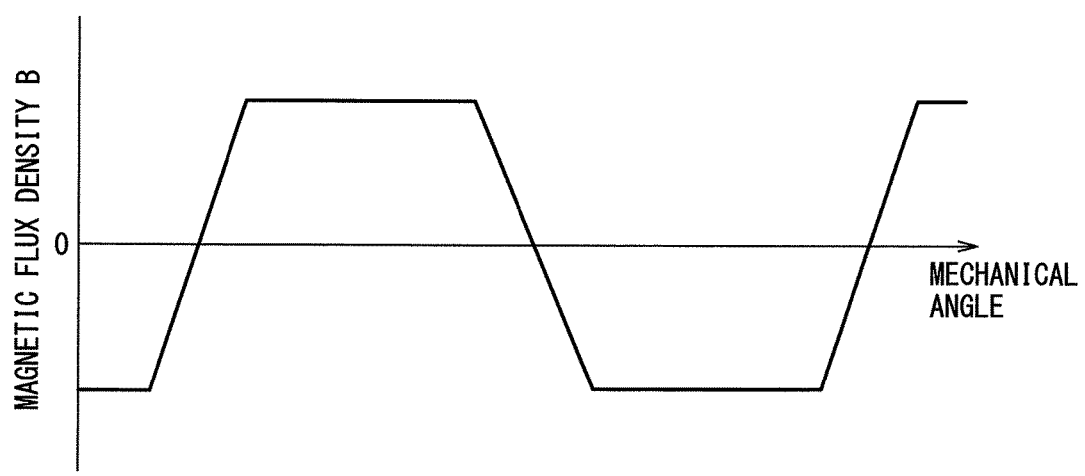
FIG. 9B is a diagram illustrating a waveform of a magnetic flux density generated from the rotor illustrated in FIG. 9A.
Figure 10:
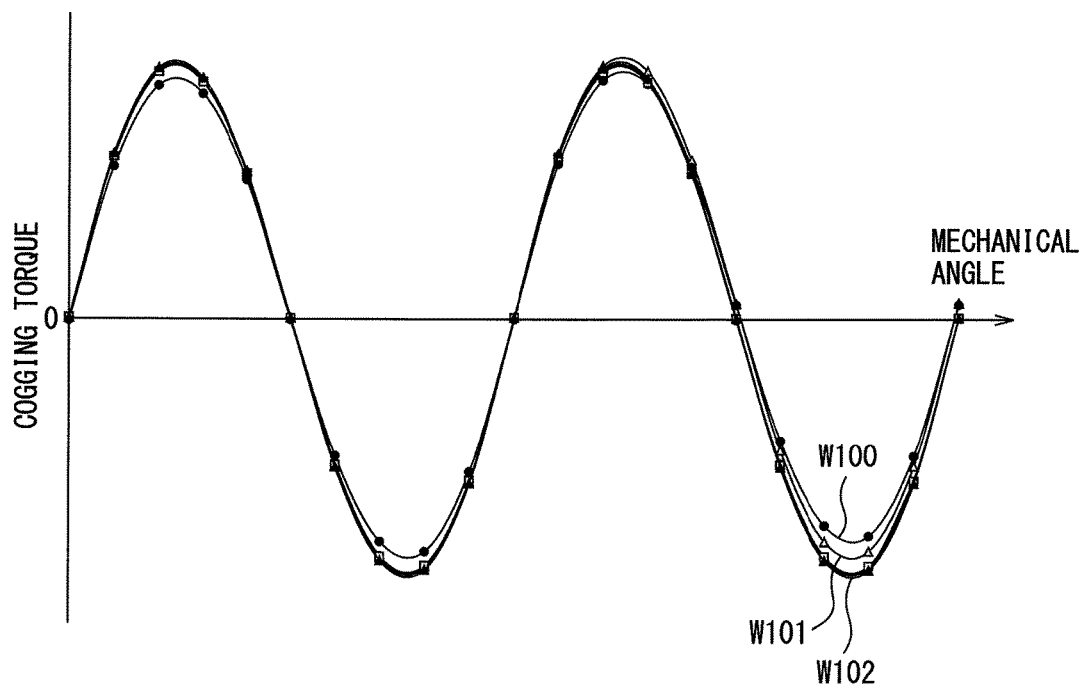
FIG. 10 is a diagram illustrating a change in waveform of cogging torque generated in the electric motor having the outer peripheral surface shape illustrated in FIG. 9A.

In the case of the trapezoidal wave, no magnetic flux concentrates at magnetic pole centers (illustrated in FIG. 9B). Thus, as illustrated in FIG. 10, a reduction effect of cogging torque is not obtained even if correction is performed to form concave parts at the magnetic pole central parts. On the other hand, in the case of the sine wave as in the embodiment, the magnetic flux concentrates at the magnetic pole central parts 12. Thus, by forming the tiny concave parts 15 at the magnetic pole central parts 12, magnetic coenergy can be adjusted, and the cogging torque can be reduced.

(2) When the maximum correction amount "d" is set, for example, equal to or less than 0.1 mm, or about 1/100 of the stator inner diameter "a", the correction amount ΔR is very small, and the magnitude of the cogging torque can be adjusted according to the maximum correction amount "d" without changing the cycle of the cogging torque. In other words, when the magnetic pole center 12 where the magnetic flux concentrates is formed into a concavo-convex shape of about several mm in height, an influence on the magnetic pole unit is large, thus causing a change of the cycle of the cogging torque. On the other hand, when the maximum correction amount "d" is very small, a shape change of the magnetic pole unit is little, and only the magnitude of the cogging torque can be appropriately adjusted.

(3) The shape of the outer peripheral surface 11 of the magnetic pole unit, in other words, the radius R from the rotor rotational center P0 to the outer peripheral surface 11, is set by adding the radial direction correction amount ΔR to the reference surface 11A bulged to the radial direction outside so that the waveform of the magnetic flux density B generated from the rotor 1 exhibits the sine wave shape. Thus, shape setting of the outer peripheral surface 11 is easy.

(4) The concave part 15 is formed to have a smooth curve at the magnetic pole central part 12. Thus, without any sudden change of the shape of the outer peripheral surface 11 in the circumferential direction, fluctuation of the magnetic coenergy caused by the presence of the concave part 15 can be suppressed.

(5) The correction amount ΔR is set based on the function using, as the parameter, the phase in which the circumferential-direction center of the magnetic pole unit is 0°, in other words, the function using, as the parameter, the mechanical angle θ from the reference line L0 passing through the magnetic pole center P0. Thus, setting of the correction amount ΔR changed with the increase of the mechanical angle θ is easy.

(6) The correction amount ΔR is set by using the sine function. Thus, the concave part 15 with a smooth shape can be easily formed at the magnetic pole central part 12.

(7) When the least common multiple of the number of magnetic poles and the number of slots is increased (e.g., larger than 100), the cycle of the cogging torque is shortened to enable reduction of the magnitude of the cogging torque, but the number of slots 20 or magnets 3 increases. In this regard, according to the embodiment, the cogging torque is reduced by forming the tiny concave part 15 at the magnetic pole central part 12. This eliminates the necessity of increasing the least common multiple of the number of magnetic poles and the number of slots (in the embodiment, least common multiple is 24), and the number of slots 20 or magnets 3 can be reduced.

(Modified Example)

In the above embodiment, the correction amount ΔR of the outer peripheral surface 11 of the magnetic pole unit in the radial direction is set by using the sine function. However, the correction amount ΔR can be set by using a cosine function or a hyperbolic cosine function. For example, the rotor radius R of the reference surface 11A may be given by the above formula (I), and a rotor radius R after correction may be set by the following formula (III):

$$R = a - (b-d)/\cos(c\theta) + d/\cos h(e\theta) \quad \text{(III)}$$

In the formula (III), $1/\cos h(0)=1$ is satisfied when $\theta=0$. Accordingly, to match a minimum gap "b" after correction with a minimum gap "b" of the reference surface 11A, $1/\cos(c\theta)$ is multiplied not by a coefficient "b" but by a coefficient $(b-d)$.

Figure 11:
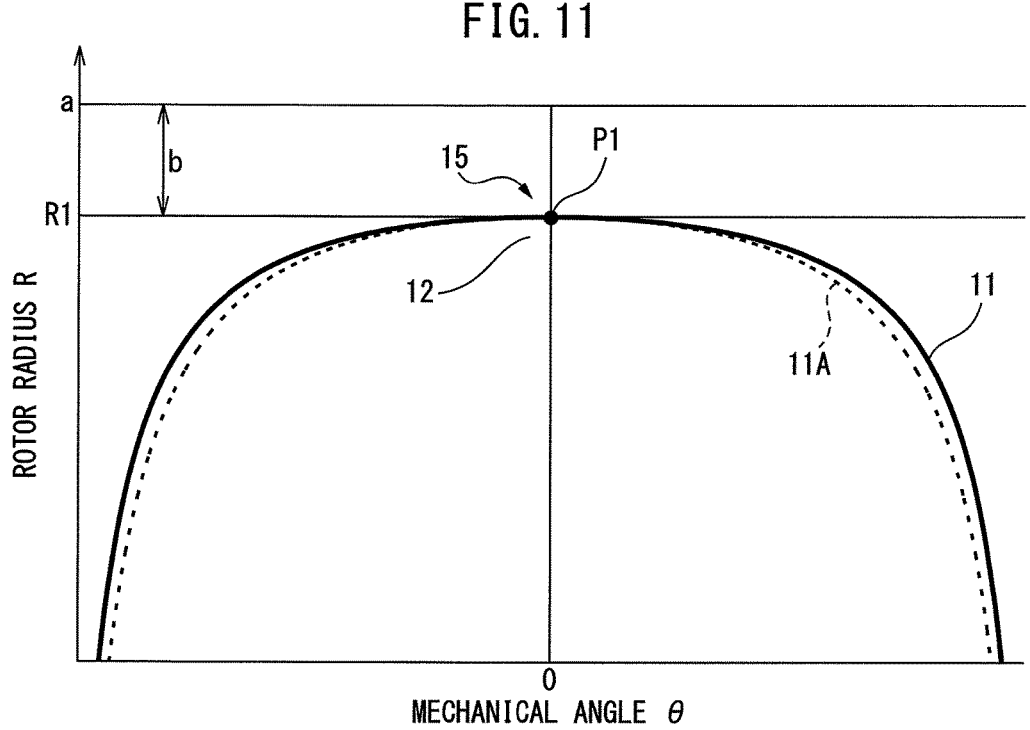
FIG. 11 is a diagram illustrating a modified example of the electric motor illustrated in FIG. 6.

FIG. 11 is an enlarged view illustrating an outer peripheral shape of the yoke 10 obtained by the above formula (III). A dotted line in FIG. 11 is, as in the case illustrated in FIG. 6, a rotor radius R of the reference surface 11A. As indicated by a solid line in FIG. 11, a tiny concave part 15 is formed at the magnetic pole central part 12. A correction amount ΔR at the magnetic pole center P1 is 0, and the minimum gap "b" is not changed before and after correction.

Figure 12:
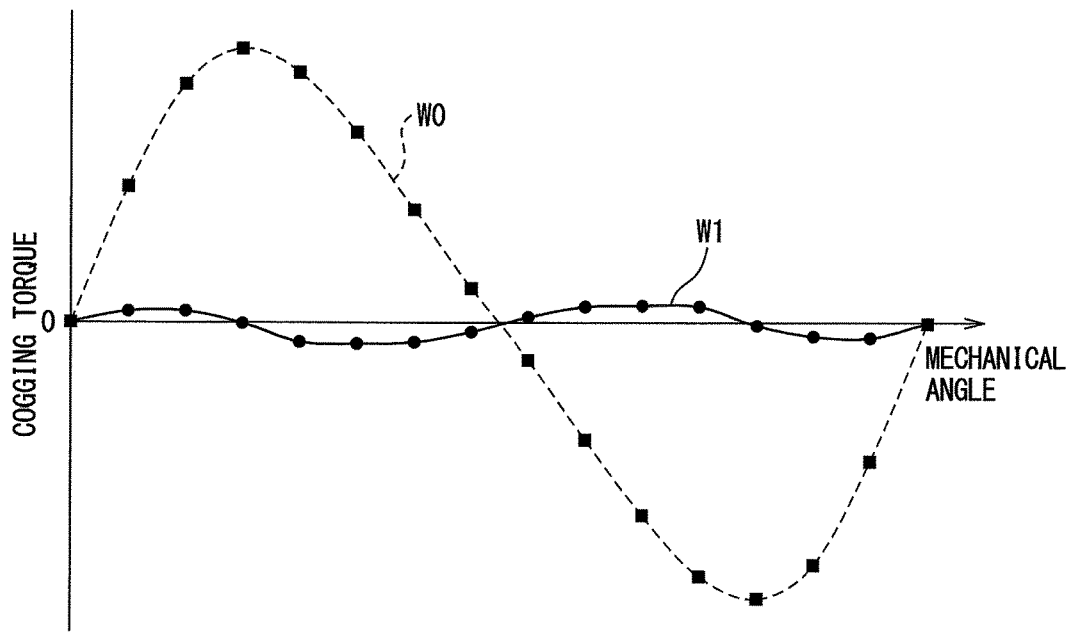
FIG. 12 is a diagram illustrating change in waveforms of cogging torque generated in the electric motor having an outer peripheral surface shape illustrated in FIG. 11.

FIG. 12 is a diagram illustrating a waveform of cogging torque when the outer peripheral surface 11 of the rotor 1 is configured as illustrated in FIG. 11. In FIG. 12, W0 and W1 are respectively a waveform when no correction is performed for the reference surface 11A (indicated by the dotted line in FIG. 11) and a waveform when correction is performed (indicated by the solid line in FIG. 11). As illustrated in FIG. 12, the cogging torque indicated by the waveform W1 is smaller than that indicated by the waveform W0. Thus, a magnitude of the cogging torque can be reduced by adding the correction amount ΔR to the rotor radius R of the reference surface 11A to form the tiny concave part 15 at the magnetic pole central part 12.

Figure 13:
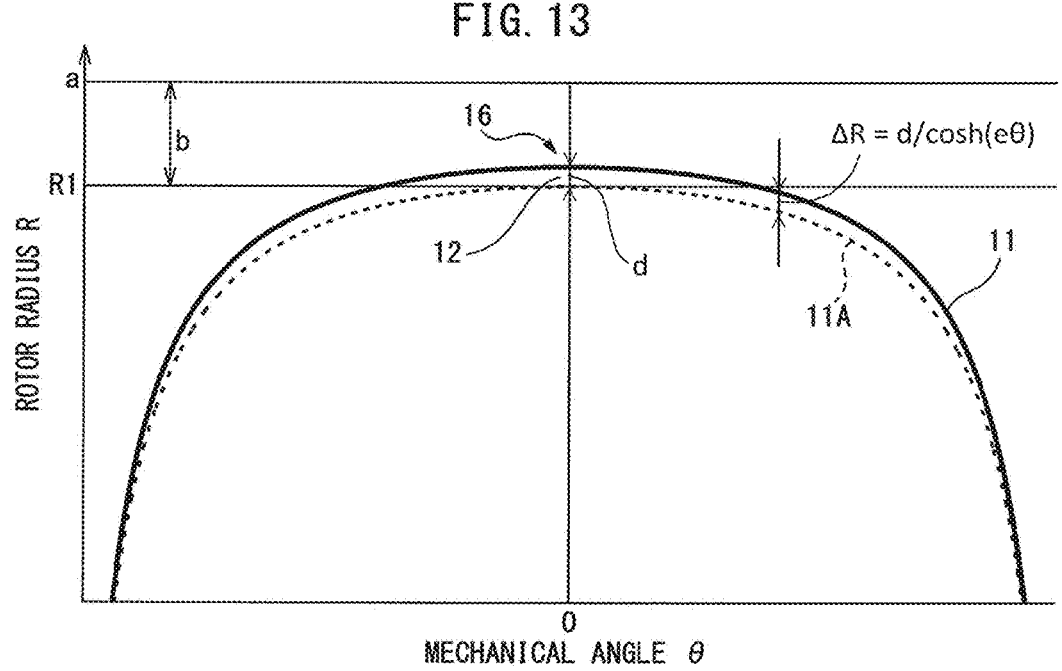
FIG. 13 is a diagram illustrating another modified example of the electric motor illustrated in FIG. 6.

In the above embodiment, the tiny concave part 15 is formed at the magnetic pole central part 12 of the rotor 1. However, a tiny convex part may be formed instead. FIG. 13 is a diagram illustrating an example where a tiny convex part 16 is formed. In FIG. 13, a rotor radius R (indicated by a solid line in FIG. 13) is set by the following formula (IV):

$$R = a - b/\cos(c\theta) + d/\cos h(e\theta) \quad \text{(IV)}$$

In this case, $1/\cos h(0)=1$ is satisfied when $\theta=0$. Thus, the rotor radius R is larger by a maximum correction amount "d" than that of the reference surface 11A, and a minimum gap is accordingly smaller by a corresponding amount. However, because the maximum correction amount "d" is very small, a changing amount of the minimum gap is small, causing no problem for gap setting for rotor rotation. When the tiny convex part 16 is formed at the magnetic pole central part 12, the minimum gap after correction may be matched with the minimum gap "b" before correction.

Figure 14:
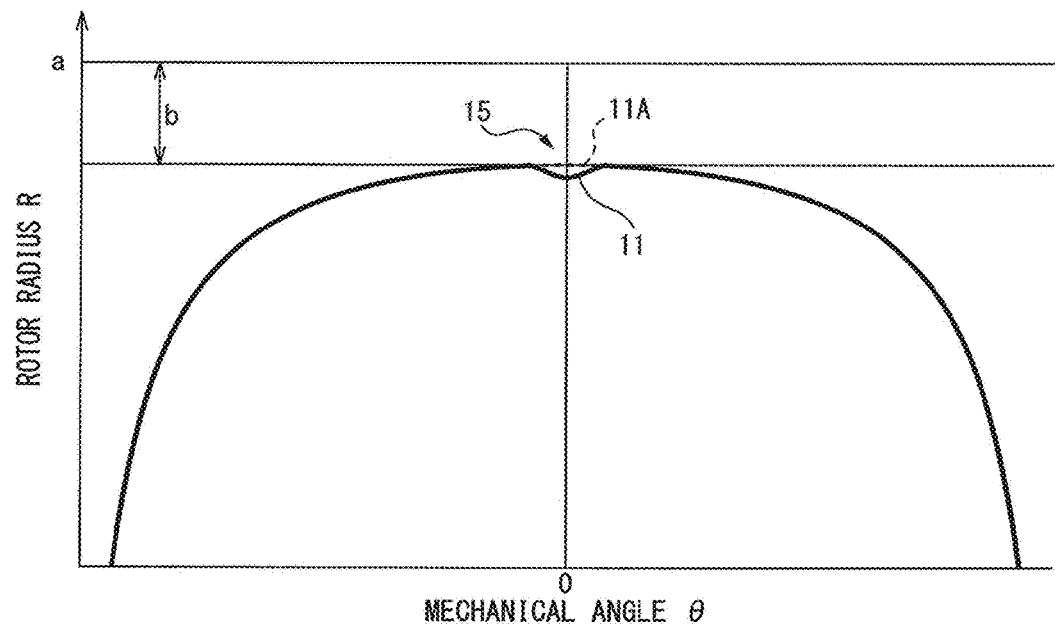
FIG. 14 is a diagram illustrating further modified example of the electric motor illustrated in FIG. 6.

The tiny concave part 15 or the tiny convex part 16 may be formed at the magnetic pole central part 12 by using a spline function. FIG. 14 is a diagram illustrating an example where a tiny concave part is formed at the magnetic pole central part 12 by using the spline function. The spline function is obtained by arbitrarily providing a sequence of points and sequentially connecting the points. For example, when the concave part 15 is formed by using the sine function, the sequence of points may be given along a sine curve and the points may be connected by the spline function.

Figure 15A:
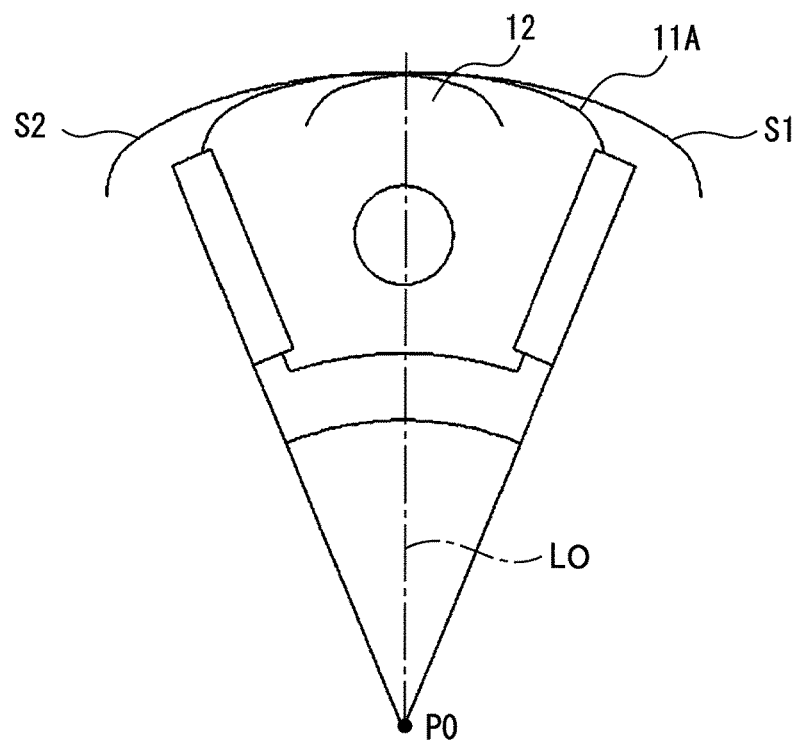
FIG. 15A is a diagram describing a method for setting of an outer peripheral surface shape of a rotor.
Figure 15B:
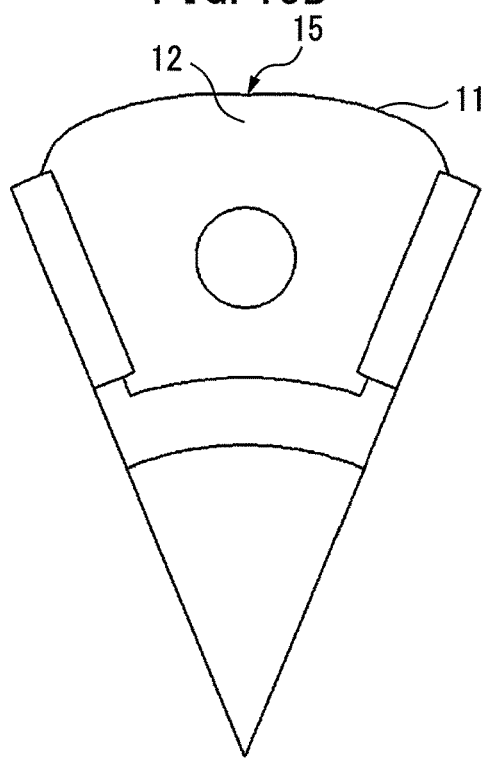
FIG. 15B is an enlarged view illustrating the outer peripheral surface shape of the rotor obtained by the method illustrated in FIG. 15A.

The tiny concave part 15 or the tiny convex part 16 may be formed at the magnetic pole central part 12 without using any of the aforementioned functions. For example, as illustrated in FIG. 15A, the reference surface 11A is rotated clockwise by only a predetermined angle θ1 (e.g., 10°) around the rotational center P0 of the rotor 1 to obtain a first curved surface S1. In addition, the reference surface 11A is rotated anticlockwise by only a predetermined angle −θ1 to obtain a second curved surface S2. Alternatively, the first curved surface S1 is symmetrically folded at the axis L0 to obtain the second curved surface S2. By smoothly connecting the first curved surface S1 and the second curved surface S2 at the magnetic pole central part 12, the tiny concave part 15 can be formed as illustrated in FIG. 15B.

As apparent from the foregoing, the most remarkable feature of the present invention is that the tiny concave part 15 or the tiny convex part 16 is formed at the magnetic pole central part 12. In this case, "tiny" means a size enough to prevent changing of the waveform cycle of the cogging torque determined by the least common multiple of the number of slots 20 and the number of magnetic poles of the rotor 1. For example, such size includes a depth of 0.1 mm or less for a concave part or a height of 0.1 mm or less for a convex part. Sizes of the concave part 15 and the convex part 16 are preferably set according to the outer diameter of the rotor 1 or the size of the minimum gap "b" instead of setting uniformly ignoring the size of the electric motor.

Figure 16:
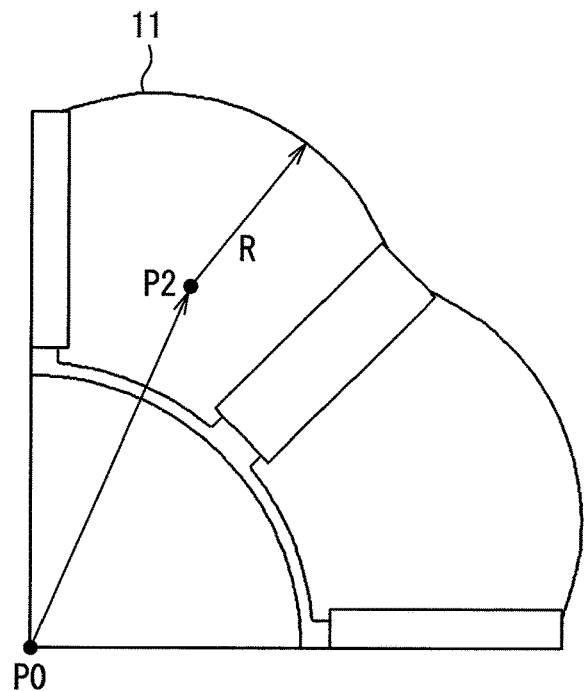
FIG. 16 is a diagram illustrating further modified example of the electric motor illustrated in FIG. 6.

In the embodiment, the shape of the outer peripheral surface 11 of the rotor 1 is set based on the distance R from the rotational center P0 of the rotor 1. However, for example, as illustrated in FIG. 16, the shape (reference surface 11a and correction amount ΔR) of the outer peripheral surface 11 of the rotor 1 may be set based on a distance R from a point P2 offset from the rotational center P0. In other words, a reference point P2 that is a reference for shape setting of the outer peripheral surface 11 may be set at a position shifted from the rotational center P0.

Figure 17:
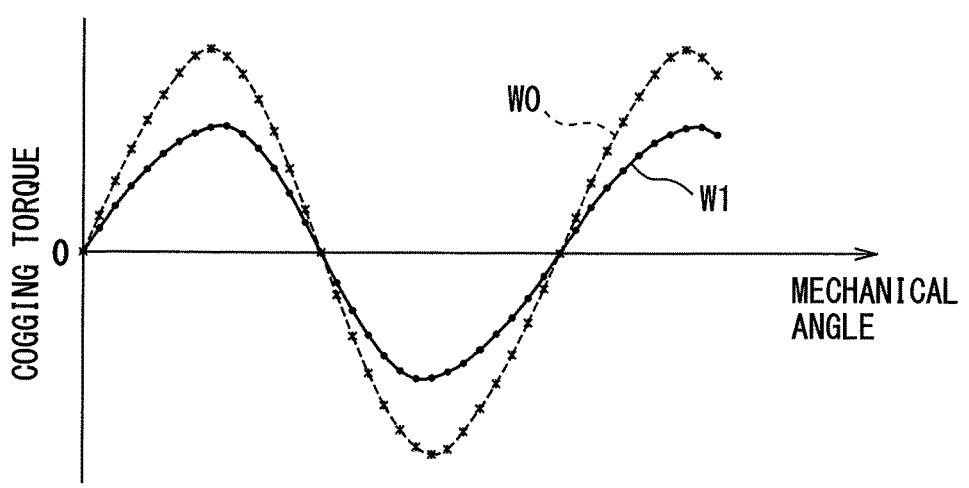
FIG. 17 is a diagram illustrating a change in waveform of cogging torque generated in the electric motor having an outer peripheral surface shape illustrated in FIG. 16.

FIG. 17 is a diagram illustrating a waveform of cogging torque with respect to the outer peripheral surface 11 illustrated in FIG. 16. In FIG. 17, W0 is a waveform when the reference surface 11a is an outer peripheral surface 11, and W1 is a waveform when the outer peripheral surface 11 is set by adding a correction amount ΔR to the reference surface 11a to form the tiny concave part 15 at the magnetic pole central part 12. As illustrated in FIG. 17, even when the reference point P2 of the outer peripheral surface 11 is not at the rotational center P0, the cogging torque can be reduced by forming the tiny concave part 15 at the magnetic pole central part 12.

Figure 18:
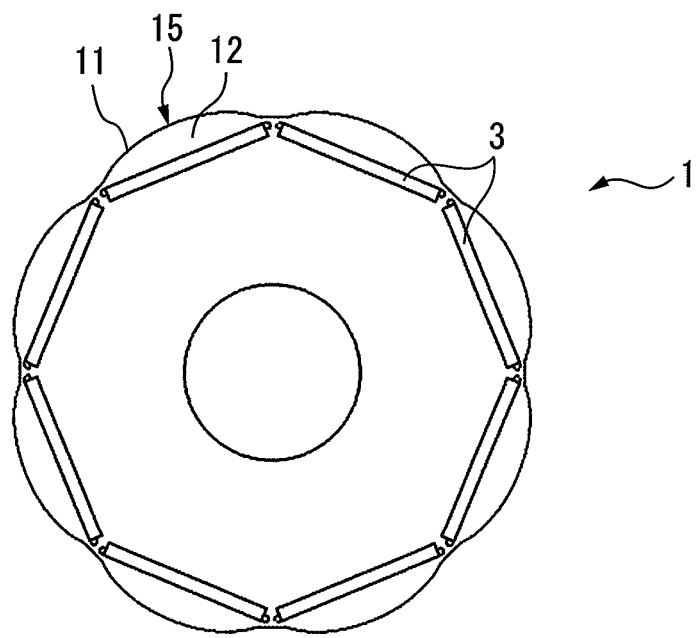
FIG. 18 is a diagram illustrating a modified example of the electric motor illustrated in FIG. 2A.
Figure 19:
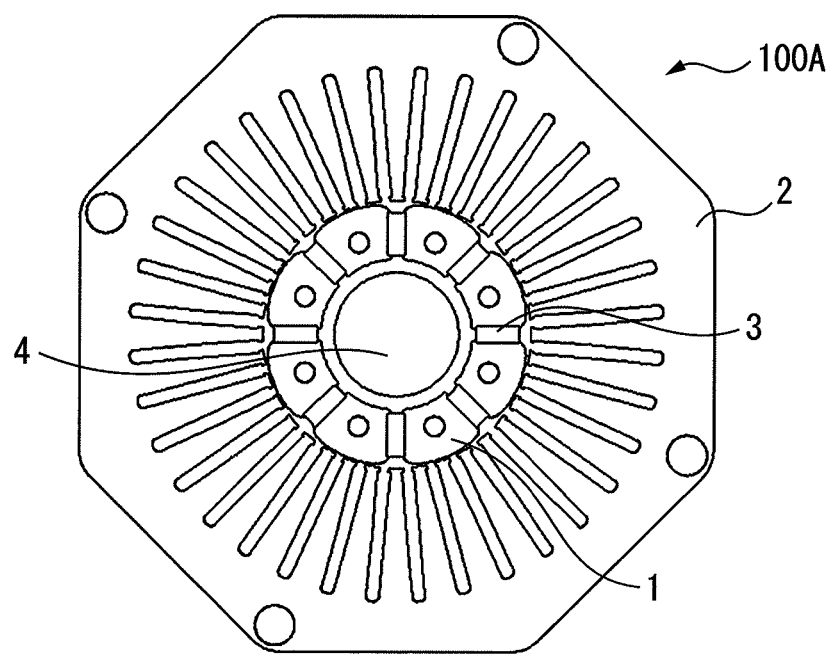
FIG. 19 is a diagram illustrating a modified example of the electric motor illustrated in FIG. 1.

In the above embodiment, the magnets 3 are radially arranged in the rotor 1 to form the magnetic pole units (illustrated in FIG. 2A). However, the arrangement of the magnets 3 is not limited to this as long as the magnetic pole units are bulged to the outside in the radial direction so that the waveform of the magnetic flux density B generated from the rotor 1 is a sine wave shape. For example, as illustrated in FIG. 18, the magnets 3 may be buried along the circumferential direction of the rotor 1 to constitute an internal buried rotor 1. Alternatively, the magnets may be stuck to a surface of the rotor 1. In the example illustrated in FIG. 18, an outer peripheral surface 11 of the rotor 1 is set by using a hyperbolic cosine function (cos h function). In this case, as in the case illustrated in FIG. 17, cogging torque can be reduced by forming a tiny concave part 15 at the magnetic pole central part 12.

Figure 20:
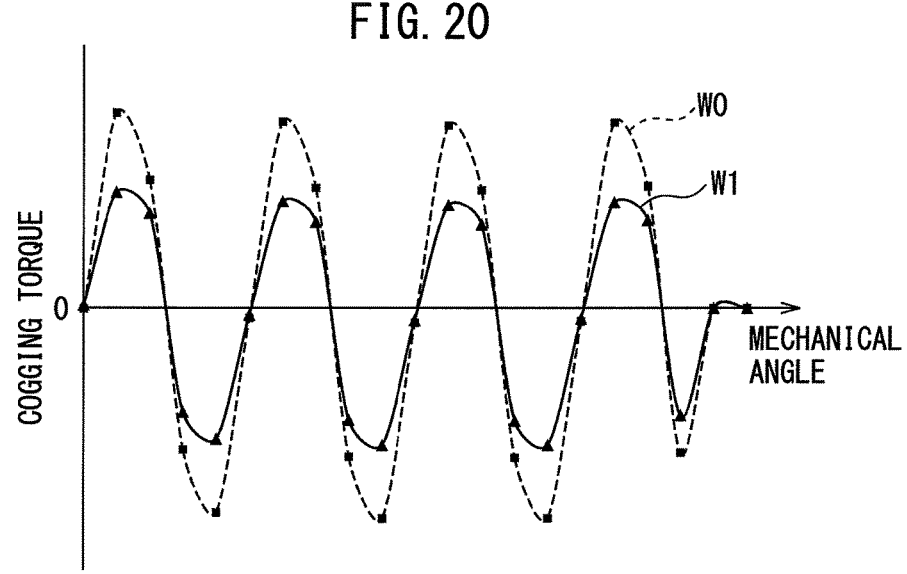
FIG. 20 is a diagram illustrating a change in waveform of cogging torque generated in the electric motor illustrated in FIG. 19.

The embodiment has been directed to the electric motor 100 with eight poles and twelve slots. However, the number of magnetic poles and the number of slots of the electric motor to which the present invention is applied are not limited to these numbers. For example, the present invention can be similarly applied to an electric motor 100A with eight poles and thirty six slots illustrated in FIG. 19. FIG. 20 is a diagram illustrating a waveform of cogging torque when the present invention is applied to the electric motor 100A illustrated in FIG. 19. In FIG. 20, as in the case illustrated in FIG. 7, waveforms W0 and W1 are respectively waveforms before and after tiny concave parts 15 are formed at the magnetic pole central parts 12. As illustrated in FIG. 20, the cogging torque can be reduced by forming the tiny concave parts 15 at the magnetic pole central parts 12.

Figure 21:
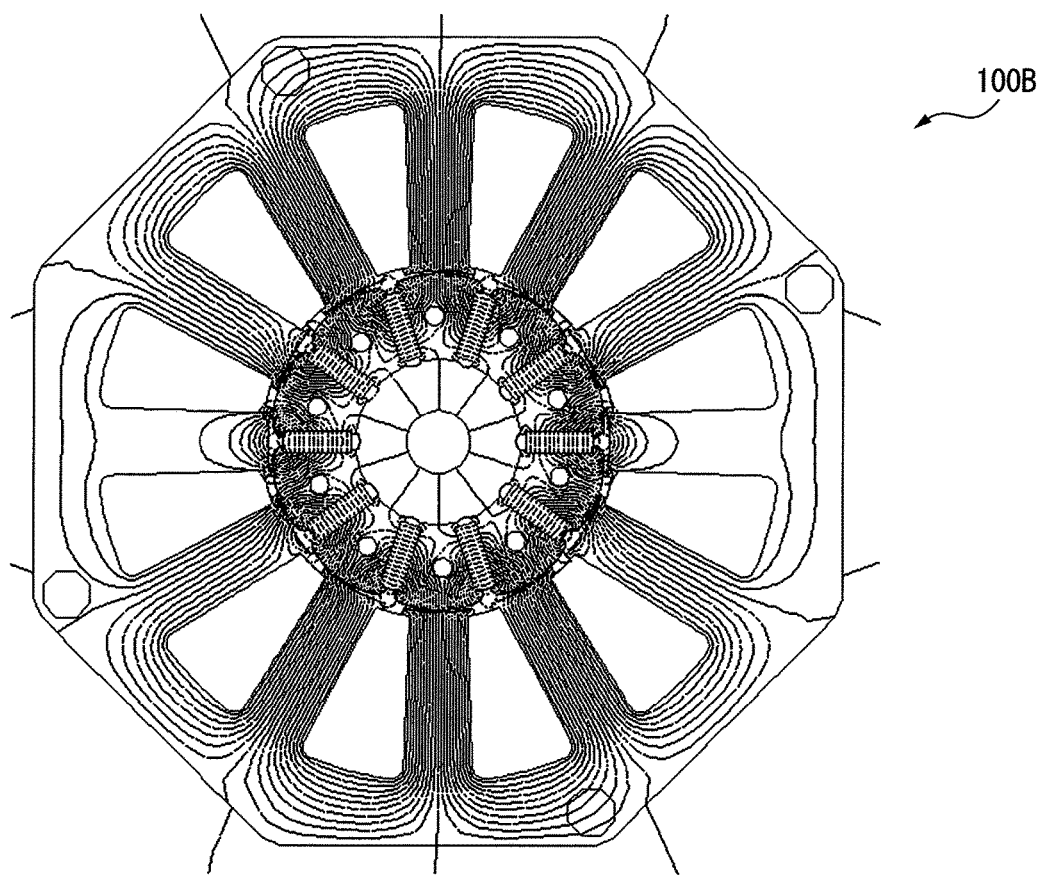
FIG. 21 is a diagram illustrating an example of magnetic flux lines in an electric motor according to further modified example of the electric motor illustrated in FIG. 1.

FIG. 21 is a diagram illustrating magnetic flux lines in an electric motor 100B with ten poles and twelve slots. The present invention can be similarly applied to the electric motor 100B with ten poles and twelve slots. A generation number of times of cogging torque per rotation of the rotor 1 is determined by a least common multiple of the number of magnetic poles and the number of slots. However, according to the present invention, the cogging torque can be reduced even without increasing the least common multiple. Thus, the least common multiple is preferably 100 or less.

The embodiment can be arbitrarily combined with one or a plurality of modified examples.

According to the present invention, the concave or convex parts are formed at the central part in the circumferential direction of the outer peripheral surfaces of the magnetic pole units, and the concave or convex parts are small enough to prevent changing of the waveform cycle of the cogging torque determined by the least common multiple of the number of slots and the number of magnetic poles of the rotor. Thus, by appropriately changing the sizes of the concave or convex parts, the magnitude of the cogging torque can be easily adjusted to an arbitrary magnitude.

While the present invention has been described with reference to the preferred embodiments thereof, it will be understood, by those skilled in the art, that various changes and modifications may be made thereto without departing from the scope of the appended claims.

The invention claimed is:

1. A method of reducing cogging torque in a synchronous electric motor comprising:
   providing a rotor including a plurality of magnetic pole units, each magnetic pole unit having the same shape wherein each magnetic pole unit has an outer peripheral surface and each of the magnetic pole units has a magnetic pole center P1; and
   providing a stator including slots facing the outer peripheral surface of the rotor, wherein,
   correcting the outer peripheral surface of each of the magnetic poles by adding a correction amount based on a sine function to a reference surface to create a corrected outer peripheral surface, the reference surface having a rotor radius given by:

$R = a - b/\cos(c\theta)$ and the correction amount is given by:

$\Delta R = d \sin(e\theta)$, wherein, the corrected outer peripheral surface has a rotor radius given by:

$R + \Delta R = a - b/\cos(c\theta) + d \sin(e\theta)$, wherein,
   a is a radius of an inner peripheral surface of the stator,
   b is a minimum gap between the rotor and the stator,
   c is a coefficient,
   θ is a mechanical angle between about −7.5° and about 7.5°,
   d is a maximum correction amount, and
   e is a coefficient set so that eθ is about 180° when the mechanical angle is at its maximum value and about −180° when the mechanical angle is at its minimum value,
   wherein the corrected outer peripheral surface of each of the magnetic pole units is bulged to an outside in a radial direction so that a waveform of a magnetic flux density generated from the rotor is a sine wave shape, and a concave part is formed at a central part in a circumferential direction of an outer peripheral surface in each of the magnetic pole units, the concave part being small enough to prevent changing of a waveform cycle of cogging torque determined by a least common multiple of the number of slots and the number of magnetic poles of the rotor.

2. The method according to claim 1, wherein the least common multiple of the number of magnetic poles of the rotor and the number of slots is equal to or less than 100.

3. A method of reducing cogging torque in a synchronous electric motor comprising:
providing a rotor including a plurality of magnetic pole units, each magnetic pole unit having the same shape wherein each magnetic pole unit has an outer peripheral surface and each of the magnetic pole units has a magnetic pole center P1; and
providing a stator including slots facing the outer peripheral surface of the rotor, wherein,
correcting the outer peripheral surface of each of the magnetic poles by adding a correction amount based on a hyperbolic cosine function to a reference surface to create a corrected outer peripheral surface, the reference surface having a rotor radius given by:

$$R = a - b/\cos(c\theta)$$

and the correction amount is given by:

$$\Delta R = d/\cos h(e\theta)$$

wherein, the corrected outer peripheral surface has a rotor radius given by:

$$R + \Delta R = a - b/\cos(c\theta) + d/\cos h(e\theta)$$

wherein,
a is a radius of an inner peripheral surface of the stator,
b is a minimum gap between the rotor and the stator,
c is a coefficient,
$\theta$ is a mechanical angle between about $-7.5°$ and about $7.5°$
d is a maximum correction amount, and
e is a coefficient set so that $e\theta$ is about 180° when the mechanical angle is at its maximum value and about $-180°$ when the mechanical angle is at its minimum value,
wherein the corrected outer peripheral surface of each of the magnetic pole units is bulged to an outside in a radial direction so that a waveform of a magnetic flux density generated from the rotor is a sine wave shape, and
a convex part is formed at a central part in a circumferential direction of an outer peripheral surface in each of the magnetic pole units, the convex part being small enough to prevent changing of a waveform cycle of cogging torque determined by a least common multiple of the number of slots and the number of magnetic poles of the rotor.

4. The method according to claim 3, wherein the least common multiple of the number of magnetic poles of the rotor and the number of slots is equal to or less than 100.

* * * * *